(12) United States Patent
Matoba et al.

(10) Patent No.: US 6,590,955 B2
(45) Date of Patent: Jul. 8, 2003

(54) OPEN CHAMBER-TYPE X-RAY ANALYSIS APPARATUS

(75) Inventors: Yoshiki Matoba, Chiba (JP); Mitsuo Naito, Chiba (JP); Koichi Tamura, Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 09/827,124

(22) Filed: Apr. 5, 2001

(65) Prior Publication Data

US 2001/0028698 A1 Oct. 11, 2001

(30) Foreign Application Priority Data

Apr. 6, 2000 (JP) ........................................ 2000-104848
Feb. 23, 2001 (JP) ........................................ 2001-048261

(51) Int. Cl.⁷ .......................................... G01N 23/223
(52) U.S. Cl. ............................... 378/44; 378/48; 378/80
(58) Field of Search .............................. 378/44, 45, 46, 378/47, 48, 49, 80

(56) References Cited

U.S. PATENT DOCUMENTS

| 5,832,054 A | * | 11/1998 | Kuwabara | ..................... 378/45 |
| 6,233,307 B1 | * | 5/2001 | Golenhofen | ................. 378/44 |
| 6,314,158 B1 | * | 11/2001 | Shiota et al. | ................. 378/48 |

* cited by examiner

*Primary Examiner*—Drew A. Dunn
(74) *Attorney, Agent, or Firm*—Adams & Wilks

(57) ABSTRACT

An open chamber-type X-ray fluorescence analysis apparatus is provided to analyze a large-sized sample located outside the open chamber. The apparatus has a helium inlet provided in the open chamber for injecting helium gas into the chamber to replace gas within the chamber with helium, a film attaching/removing mechanism for covering the opening in the chamber with a film having high transmittance with respect to X-rays, and a gas outlet provided in the chamber for allowing gas to exit the chamber.

4 Claims, 3 Drawing Sheets

CURVED TYPE

FLAT TYPE

OPEN CHAMBER-TYPE X-RAY ANALYSIS APPARATUS

BACKGROUND OF THE INVENTION

The present invention relates to a X-ray fluorescence analysis apparatus for detecting secondary X-rays generated by a sample during irradiation with X-rays and carrying out elementary analysis.

An open chamber-type analysis apparatus is used for performing qualitative and quantitative analysis on materials that lie outside of an open part (surrounding the primary X-rays) of the chamber, i.e. large materials and unmovable materials that cannot be housed within a normal X-ray fluorescence analysis apparatus.

When analysis of light elements within a material is performed using the open chamber-type X-ray fluorescence analysis apparatus, fluorescent X-rays from the light elements are absorbed by the sample and by the N2 and O2 in the atmosphere within the detector, which makes it difficult to obtain a sufficient intensity of X-rays.

SUMMARY OF THE INVENTION

In order to resolve the aforementioned problems, an open chamber-type x-ray fluorescence analysis apparatus having an X-ray source, X-ray detector, and an open chamber is provided with a helium inlet provided at the open chamber for replacing gas within the chamber, a light element film attaching/removing mechanism provided at an open section of the open chamber and having high transmittance with respect to X-rays, and a gas outlet within the chamber. Gas that substantially absorbs X-rays of low energy is then replaced with helium having a low absorption rate by allowing helium gas to flow from the inlet. A stable state can be attained within a short period of time by gradually expelling air within the chamber to outside of the chamber via a space in the threaded section of the film attaching/detaching mechanism. This enables stable qualitative and quantitative analysis of light elements within the sample at this open chamber-type X-ray fluorescence analysis apparatus.

Further, a ring-shaped jig having an O-ring and a mechanism for pulling the O-ring may be employed as the light element film attaching/removing mechanism.

Moreover, the light element film attaching/detaching mechanism and the gas outlet within the chamber are formed in an integral manner.

The light element film attaching/removing mechanism may be formed integrally with a collimator limiting a range of passage of the X-rays.

DETAILED DESCRIPTION OF THE PREFERRED EMBODIMENT

Figure 1:
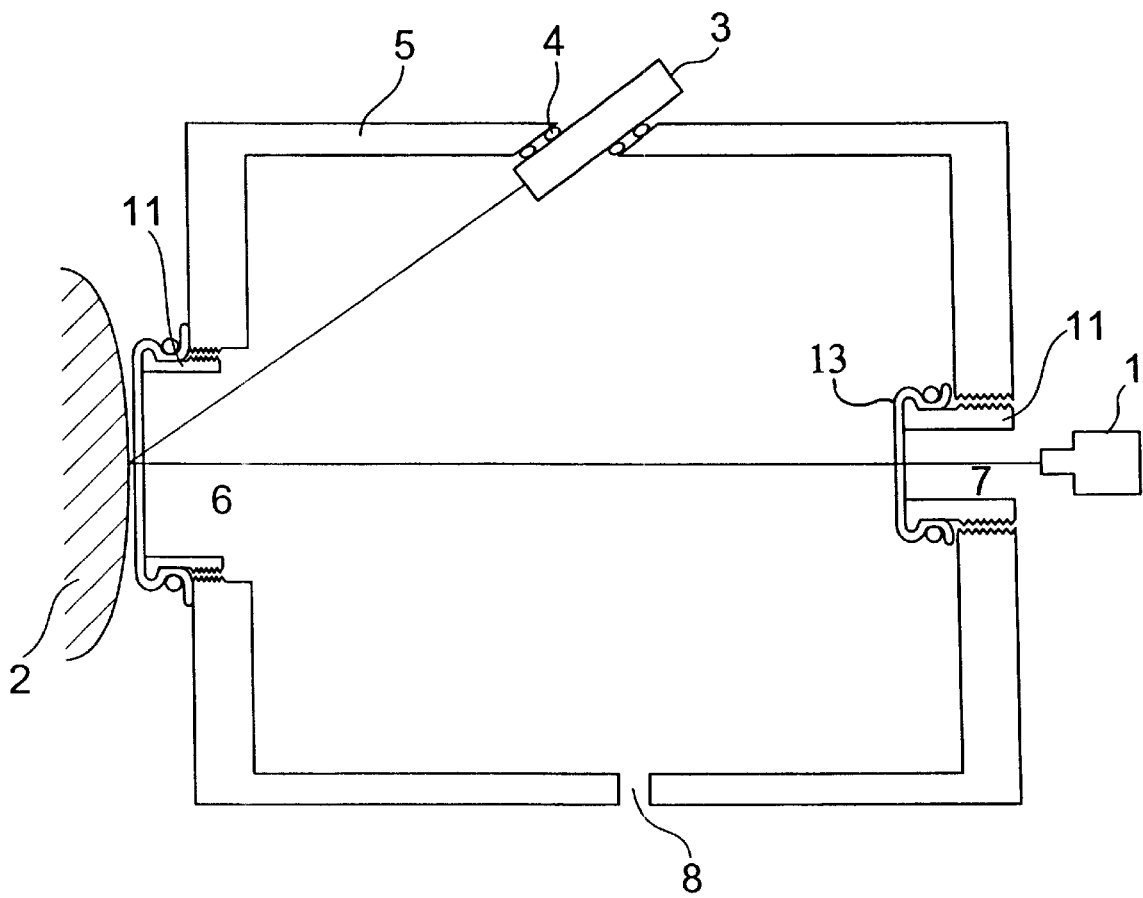
FIG. 1 is an outline view showing a helium replacement mechanism in an open chamber of the present invention.

The following is a description, based on FIG. 1, of a preferred embodiment of the present invention.

X-rays irradiated from an X-ray source 1 are incident to a sample 2. Secondary X-rays such as X-ray fluorescence are then generated by the sample 2 and detected by an X-ray detector 3. The detector 3 is fitted to a detector fitting opening by an O-ring 4 etc. so as to be held in an air tight manner so that gas within the chamber cannot escape from the chamber. The open chamber 5 has openings at a sample neighboring section 6 and an X-ray source emitter 7, with a thread being formed on the insides of these open sections.

Figure 2:
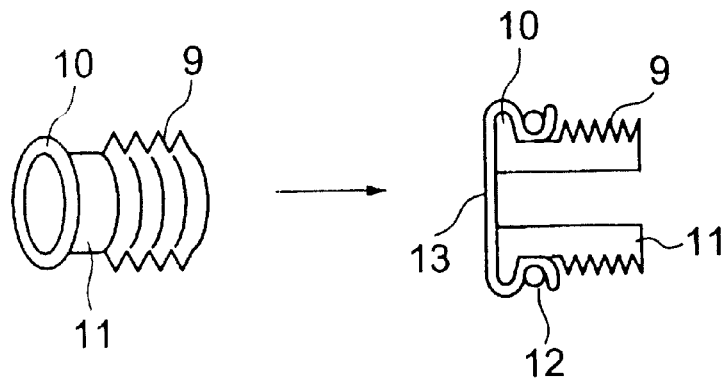
FIG. 2 is an outline view showing a light element film detaching mechanism in a open chamber of the present invention.

A helium gas inlet 8 is provided at the open chamber 5. When it is wished to analyze light elements in the sample, a light element film 13 is fixed to a ring-shaped jig 11 having a threaded section 9 and a lip 10 as shown in FIG. 2 using an O-ring and is fitted to the threaded part of an open section of the open chamber 5.

Figure 3A:
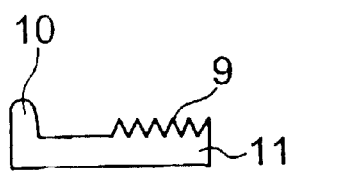
FIG. 3A is an outline view showing the shape of a link-shaped jig (curved type) in an open chamber of the present invention.
Figure 3B:
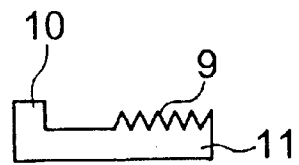
FIG. 3B is an outline view showing the shape of a link-shaped jig (flat type) in an open chamber of the present invention.

As shown in FIGS. 3A and 3B, as the ring-shaped lip 10 is for fixing to the O-ring 12, the front of the lip 10 may be curved or flat in shape. A microfilm a few μm thick may be used as the light element film 13. However, as this light element film for the surface of the sample may come in contact with the sample so as to become contaminated, or may become damaged during operation, the light element film 13 is fitted in a detachable manner to the ring-shaped jig 11 using an O-ring 12 so as to be easy to replace manually.

Helium gas is introduced into the chamber from the helium gas inlet 8. Almost all of the N2 and O2 that substantially absorbs low energy X-rays is expelled to outside of the open chamber from an intervening space between the threaded section between the open section of the chamber and the ring-shaped jig, i.e. the space between the threaded section constitutes an outlet for gas within the chamber.

By continuing to introduce helium gas, the chamber substantially fills with helium gas, with a steady state being attained within one to two minutes. As a result, it becomes difficult for low energy X-rays within the primary and secondary X-rays to be absorbed by the gas within the chamber and qualitative and quantitative analysis of the light elements within the sample can be carried out in a stable manner.

In the following there is shown the Al characteristic X-ray detection intensity when Al is analyzed as a sample when helium replacement is not performed and when helium replacement is performed for an open chamber-type X-ray fluorescence analyzing apparatus.

When He is not replaced 20 cps (K radiation for Al)
When He is replaced 470 cps (K radiation for Al)

Figure 4:
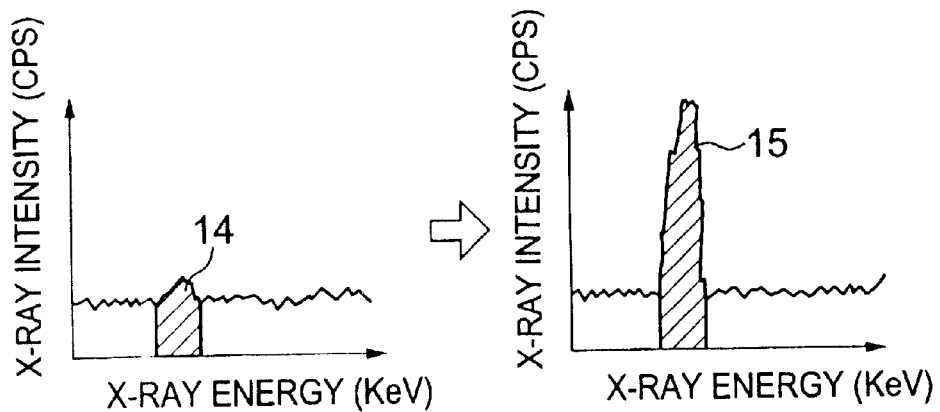
FIG. 4 is a graph showing a characteristic X peak of a light element.

This increases the detection intensity by 20 times or more. In the case of the open chamber-type X-ray fluorescence analyzing apparatus where He is not replaced, it is not possible to qualitatively analyze the light elements, because the peak 14 of a characteristic X-ray of a light element such as the K-radiation of Al as shown in FIG. 4 is the same as the background radiation.

However, a peak 15 of the characteristic X-rays of light elements such as K radiation etc. of Al can be made sufficiently large with respect to the background by providing a He replacement function. It is therefore also possible to qualitatively analyze light elements with large samples that cannot be contained within a related sample chamber. Further, quantitative calculations are also possible for the light elements by taking into consideration the material and thickness of the light element film. It is also possible to shorten the quantitative time and increase precision.

Figure 5:
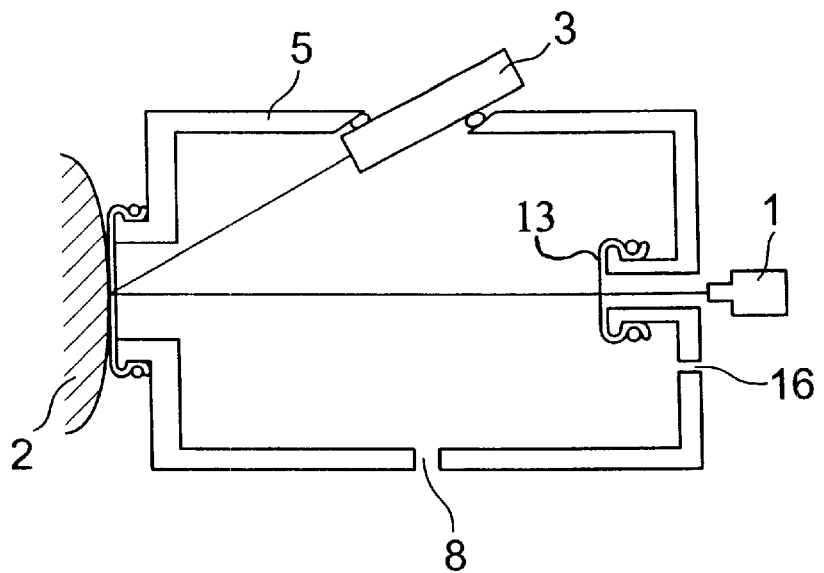
FIG. 5 is an outline view showing that having an atmospheric outlet for a helium replacement mechanism of an open chamber of the present invention.

As shown in FIG. 5, it is also possible to provide the removable light element film in a completely air-tight manner using some kind of method such as an O-ring (including non-removable states) and provide an appropriate outlet 16 within the chamber to the atmosphere. Further, there are often cases with this kind of open chamber-type X-ray fluorescence analyzing apparatus where inclination of the measuring head is changed depending on the subject being measured. However, it is necessary to make the outlet 16 within the chamber to the atmosphere small and to forcibly introduce the He so that He replacement is stable in all directions.

However, a collimator is often used with this kind of X-ray fluorescence analysis apparatus in order to limit the range of irradiation of the sample with X-rays.

Figure 6:
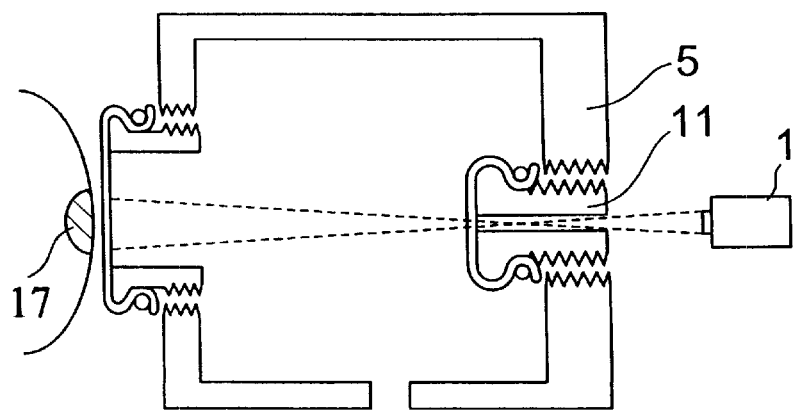
FIG. 6 is an outline view showing a collimator function of a link-shaped jig in an open chamber of the present invention.

By selecting the inner diameter of the ring-shaped jug 11, as shown in FIG. 6, the jig may be utilized as a collimator limiting a region of irradiation 17 of the sample with x-rays from the x-ray source emitter 7. In addition to being circular, it is also possible for the inside of the jig utilized as a collimator to be rectangular or angular in shape. This makes it possible to analyze an arbitrary region of the sample. By forming the removable light element film and collimator integrally, operability when changing the film and collimator can be improved, the structure can be simplified, and the apparatus can be made smaller.

Various methods other than the screw attachment method in this case can also be considered for attaching and detaching the ring-shaped jig and chamber, such as a fitting method employing a resilient material or a screw-type stopping method employing screws on the marketplace.

Qualitative and quantitative analysis of large samples is therefore possible with a X-ray fluorescence analysis apparatus having an open chamber comprising a helium gas inlet for replacing gas in the open chamber, a light element film attaching/removing mechanism provided at an open section and having high transmittance with respect to X-rays, and an outlet for gas within the chamber, by providing a continuous flow of helium gas.

What is claimed is:

1. An open chamber-type X-ray fluorescence analysis apparatus comprising: an X-ray source for irradiating a sample with a primary X-ray; an X-ray detector for detecting a responsive X-ray produced in response to X-ray irradiation of the sample; an open chamber having an opening through which the primary X-ray is directed to irradiate the sample, the sample being located outside the open chamber; a helium inlet provided in the open chamber for injecting helium gas into the chamber to replace gas within the chamber with helium; a film attaching/removing mechanism for covering the opening in the open chamber with a film having high transmittance with respect to X-rays; and a gas outlet provided in the open chamber for allowing gas to exit the chamber.

2. An open chamber-type X-ray fluorescence analysis apparatus according to claim 1; wherein the film attaching/removing mechanism comprises a ring-shaped jig having an O-ring and a mechanism for pulling the O-ring.

3. An open chamber-type X-ray fluorescence analysis apparatus according to either one of claim 1 or claim 2; wherein the gas outlet is provided in the film attaching/detaching mechanism.

4. An open chamber-type X-ray fluorescence analysis apparatus according to either one of claim 1 or claim 2; wherein the film attaching/removing mechanism is formed integrally with a collimator for limiting a range of passage of the X-rays.

\* \* \* \* \*